(12) United States Patent
Noui et al.

(10) Patent No.: US 9,119,694 B2
(45) Date of Patent: Sep. 1, 2015

(54) SPECTRAL SCANNING PHOTOCROSSLINKING DEVICE

(75) Inventors: Hervé Noui, Salles d'aude (FR); Philippe Lucas, Saint Jean d'illac (FR)

(73) Assignee: SOCIETE POUR LA CONCEPTION DES APPLICATIONS DES TECHNIQUES ELECTRONIQUES, Merignac (FR)

( * ) Notice: Subject to any disclaimer, the term of this patent is extended or adjusted under 35 U.S.C. 154(b) by 0 days.

(21) Appl. No.: 13/808,441

(22) PCT Filed: Jul. 4, 2011

(86) PCT No.: PCT/FR2011/051569
§ 371 (c)(1),
(2), (4) Date: Jul. 2, 2013

(87) PCT Pub. No.: WO2012/004504
PCT Pub. Date: Jan. 12, 2012

(65) Prior Publication Data
US 2013/0273493 A1    Oct. 17, 2013

(30) Foreign Application Priority Data
Jul. 7, 2010    (FR) ..................................... 10 55509

(51) Int. Cl.
*A61C 19/00*    (2006.01)
*A61C 13/15*    (2006.01)

(52) U.S. Cl.
CPC .................................... *A61C 19/004* (2013.01)

(58) Field of Classification Search
CPC ... A61C 19/003; A61C 19/004; A61C 19/066

USPC .......................................................... 433/29
See application file for complete search history.

(56) References Cited

U.S. PATENT DOCUMENTS

| | | | | |
|---|---|---|---|---|
| 6,008,264 | A * | 12/1999 | Ostler et al. ....................... | 522/4 |
| 6,331,111 | B1 * | 12/2001 | Cao ................................... | 433/29 |
| 6,692,250 | B1 * | 2/2004 | Decaudin et al. ................ | 433/29 |
| 7,029,277 | B2 * | 4/2006 | Gofman et al. .................. | 433/29 |
| 2001/0046652 | A1 * | 11/2001 | Ostler et al. ..................... | 433/29 |
| 2003/0091955 | A1 * | 5/2003 | Burtscher et al. ............... | 433/29 |
| 2004/0076921 | A1 * | 4/2004 | Gofman et al. .................. | 433/29 |
| 2009/0322227 | A1 * | 12/2009 | Jones et al. ..................... | 315/76 |

FOREIGN PATENT DOCUMENTS

| EP | 1 410 768 A2 | 4/2004 |
|---|---|---|
| WO | 2007/066112 A1 | 6/2007 |

OTHER PUBLICATIONS

International Search Report issued in PCT/FR2011/051569, mailed Sep. 21, 2011.

* cited by examiner

*Primary Examiner* — Ralph Lewis
(74) *Attorney, Agent, or Firm* — Workman Nydegger

(57) ABSTRACT

A photo-curing device includes a light source for initiating the curing of a photo-curable material. The light source has light-emitting diodes, each emitting light in a determined wavelength range, the wavelength ranges of the LEDs overlapping partially so as to cover a continuous wavelength range that is broader than the wavelength range of each LED. An activation device is provided for selectively activating each LED.

17 Claims, 5 Drawing Sheets

SPECTRAL SCANNING PHOTOCROSSLINKING DEVICE

BACKGROUND OF THE INVENTION

The invention relates to a photo-curing device or appliance suitable for activating photo-curable matrices contained in materials for filling, reconstitution, impression-taking, adhesive bonding, or whitening, in particular for application in the field of dentistry, the device or appliance having a light source and optical and electronic means for controlling, modulating, aiming, selecting, and conveying light energy to a zone that is to be illuminated.

The photo-curing of a material consists in a chemical reaction, e.g. taking place during polymerization, that serves to bond together permanently the macromolecules that make up the material. It is induced by delivering light radiation that enables photo-initiators contained in the material to produce covalent bonds that modify the structure of the material, thus making it possible to obtain the looked-for physical properties, such as hardening of the material or adhesive bonding of the material on a support.

The effectiveness of photo-curing depends firstly on the photo-initiator and on its suitability for creating macroradicals, e.g. on polymer chains, so it must be possible to irradiate the material with wavelengths lying in the photosensitivity spectrum of the photo-initiator present in the material. However, the photo-curable materials that are used for example in the field of dentistry are progressing continuously, as are the photo-initiators included in their compositions, thereby leading to a greater diversity of sensitivity spectra that need to be taken into consideration.

In order to satisfy the needs of practitioners, photo-curing devices therefore need to generate a broad light spectrum suitable for photo-curing materials containing a variety of photo-initiators, such as camphoroquinone (CQ), phenylpropanedione (PPD), and lucirin, for which the target wavelength ranges corresponding to the sensitivity spectra are as shown in FIG. 1.

Furthermore, in most of the materials used, this chemical reaction is an exothermic reaction that causes a rise in temperature of the exposed zones, which temperature rise is made even greater since it is in addition to the temperature rise caused by light energy being absorbed by the tissues themselves.

Present devices, such as those available for dentistry, make use of two types of light source, namely:
  either a light source that emits light radiation spread over a broad spectrum, thereby satisfying the broad spectrum problem;
  or else a light source that produces radiation over a spectrum that is very narrow, or indeed monochromatic, thus limiting the amount of energy that is delivered, and thereby keeping the heating of the exposed tissues under control.

For the first category light source, the source used mainly involves halogen bulbs, arc lamps (e.g. xenon lamps), or discharge lamps.

That type of light source produces light radiation over a very broad spectrum. Nevertheless, in terms of the radiation that is useful for interacting with the photo-curable materials used, the efficiency of such sources is quite low even though their purchase price and maintenance remain expensive. Furthermore, that type of light source requires a large amount of energy for its operation associated with an active cooling device (forced convection) for dissipating the heat given off. Consequently, it is difficult to make portable devices that are powered by optionally rechargeable batteries and that use light sources of those types.

Furthermore, a non-negligible fraction of the radiation emitted by those broad spectrum sources lies in the infrared range and that can give rise to unwanted thermal effects on the tissue being treated (e.g. necroses), which effects are in addition to those of the exothermic reaction induced by the photo-curing.

Finally, a complex optical filter system needs to be implemented in order to limit the radiometric power emitted so as to avoid burning the tissue being treated by exposure to infrared radiation.

The second category includes devices making use of light-emitting diodes (LEDs). This type of light source presents the advantage of delivering a spectrum of high efficiency (providing it corresponds to the photo-curable material for treatment), since all of the energy produced is useful for the chemical reaction that is to be initiated. Devices using such sources also present low energy consumption and are consequently suitable for being powered by a self-contained power supply constituted by optionally rechargeable batteries. Their small volume enables a compact ergonomic device to be obtained. Finally, the optical devices used with this type of light source may be considerably simplified since LEDs are generally encapsulated in transparent materials presenting optimum transmission. Such materials are also molded to have a shape that enables integrated optical devices to be made that are suitable for collecting and directing the light energy produced.

Because of the narrow wavelength range covered by the emission spectrum of an LED (of the order of 20 nanometers (nm) for radiation power ≥50%), appliances fitted with only one diode cannot deliver an emission spectrum that is broad enough to initiate photo-curing of a variety of different materials.

In an attempt to remedy that drawback, an existing solution consists in increasing the energy power delivered to the LED beyond a conventional nominal value. That increases the intensity of the radiation emitted by the diode at the margins of its emission spectrum, thereby broadening its working emission spectrum. Nevertheless, under such circumstances, the overall intensity of the radiation is increased, thereby giving rise to temperature rise phenomena in tissues that patients find difficult to accept.

Furthermore, the practitioner does not always know which photo-initiators are contained in the materials being used. Thus even if a practitioner were to have a multiplicity of appliances fitted with LEDs having different emission spectra, the practitioner would still not know which one to use.

OBJECT AND BRIEF DESCRIPTION OF THE INVENTION

An object of the invention is to remedy the above-mentioned drawbacks and to provide a photo-curing lamp or device that makes it possible to cover a broad wavelength range suitable for covering the spectrum wavelength of the photo-initiator contained in the material, and to do this with a device that consumes little energy and that does not require active cooling means to be used, and with the amount of energy emitted being limited so as to control heating of the exposed tissues.

This object is achieved with a photo-curing device comprising a light source for initiating curing of a photo-curable material, in which device said light source comprises at least two light-emitting diodes each emitting light in a determined wavelength range, said wavelength ranges of said at least two LEDs overlapping partially so as to cover a continuous wavelength range that is broader than the wavelength range of a single LED, the photo-curing device further including activation means for selectively activating each LED, that is to say one LED after the other.

Thus, by using LEDs having emission spectra that cover wavelength ranges that are different but that overlap, it is possible to cover an entire broad range of wavelengths and to ensure that curing is initiated in a large number of photo-initiators, and to do so without necessarily knowing the target wavelength.

Furthermore, selectively activating each of the LEDs in the appliance of the invention serves to limit the power of the emitted radiation and the amount of energy that is consumed, e.g. in comparison with light sources making use of halogen lamps, arc lamps, or discharge lamps, while also scanning completely the broad wavelength range that is constituted by uniting the emission spectra of the LEDs.

Such advantages cannot be obtained with the diodes being activated simultaneously. Under such circumstances, the photo-curing appliance would need to be fitted with a power electronic circuit so as to enable each LED to be powered at high power while simultaneously powering all of the LEDs, and indeed powering active cooling means for limiting the amount of heat that is given off while the LEDs are being activated simultaneously.

In an aspect of the invention, the photo-curing device includes switch means for selectively powering each of said LED from a single power supply.

In another aspect of the invention, the photo-curing device includes control means for successively activating each of the LEDs at least once in a determined time interval. This ensures complete scanning of at least the broad wavelength range constituted by uniting the emission spectra of the LEDs, with this applying even in the event of an LED activation program or profile being interrupted before it has been completed.

In another aspect of the invention, the photo-curing device includes control means for successively activating each LED a plurality of times and for progressively reducing the power delivered to the LEDs. This reduces the temperature-summing phenomenon that is felt by the patient and limits the temperature stresses to which the material for curing is subjected.

According to yet another aspect of the invention, the photo-curing device includes control means for successively activating each LED over a determined activation period, the LED that emits the greatest radiation heat being activated at the beginning of the activation period and the LED that emits the least radiation heat being activated at the end of the activation period. Likewise, such control serves to better distribute the delivery of heat to the zone for treatment and thus to improve patient comfort and to limit thermal stresses.

According to a particular characteristic of the invention, the device has four LEDs having respective emission spectra centered on about 420 nm, 440 nm, 460 nm, and 480 nm so as to cover a continuous wavelength range extending from at least 410 nm to 490 nm, which range serves to initiate curing of materials containing photo-initiators such as camphoroquinone, phenylpropanedione, or lucirin.

According to another particular characteristic of the invention, the device further includes at least one waveguide for guiding and/or aiming the light radiation emitted by the LEDs towards a zone for treatment.

According to a particular aspect of the invention, the device further includes connector means suitable for receiving electrical power from at least one of the following power supplies: a self-contained power supply, mains, and a dentistry unit.

BRIEF DESCRIPTION OF THE DRAWINGS

Other characteristics and advantages of the invention appear from the following description of particular embodiments of the invention given as non-limiting examples and with reference to the accompanying drawings, in which.

DETAILED DESCRIPTION OF EMBODIMENTS OF THE INVENTION

The present invention relates to a photo-curing device for applying light radiation in a given wavelength range (emission spectra) to a photo-curable material. The term "photo-curable material" is used to designate any type of material of molecular structure that is transformed under the effect of light radiation at a given wavelength, in particular by activating photo-initiators contained in the material and giving rise to covalent bonds that modify the structure of the material (hardening, adhesion, etc.). As non-limiting examples, the photo-curable materials may in particular be composite materials for hardening such as materials for filling, reconstruction, making an impression, adhesively bonding, or materials that need to be activated such as a whitener. The invention applies particularly but not exclusively to photo-curable materials used in the field of dentistry. The invention also applies to photo-curable materials to form surface coatings in the fields of cosmetics, etc.

As described in greater detail below, the photo-curing device includes means for scanning an extended wavelength range of spectrum band corresponding to a plurality of wavelength ranges, each emitted by a respective determined LED.

Figure 2:
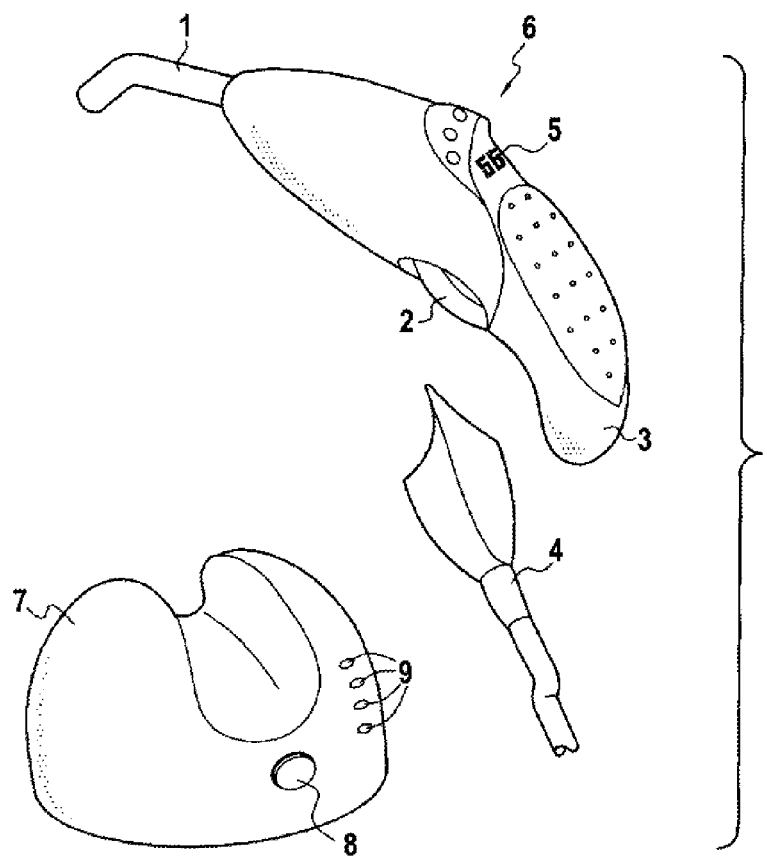
FIG. 2 is a perspective view of a photo-curing appliance in accordance with an embodiment of the invention.

FIG. 2 shows a photo-curing device in accordance with an embodiment of the invention for the purpose of photo-curing reconstitution and impression materials such as the composites used in particular in the field of dentistry. The device is constituted by a handpiece 6 having a removable sterilizable light guide 1 at its end. The device is also provided with a power supply connector that is connected either to a removable rechargeable battery 3 or to an external power supply corresponding to a mains power supply or to a power supply of a module suitable for incorporating in a dentist's chair, with the end 4 thereof plugging into the place for the removable battery 3. An operator interface 5 serves to select and display prerecorded activation profiles or programs. Activation is performed by means of a trigger 2. A recharger base 7 serves to recharge the battery 3. This recharger base includes means for monitoring the light power emitted, the user inserting the end of the light guide 1 into an inlet window of an optical sensor 8, with the emitted level of light power being displaced for example on a display screen, or on an analog scale of indicator lights 9.

Figure 3:
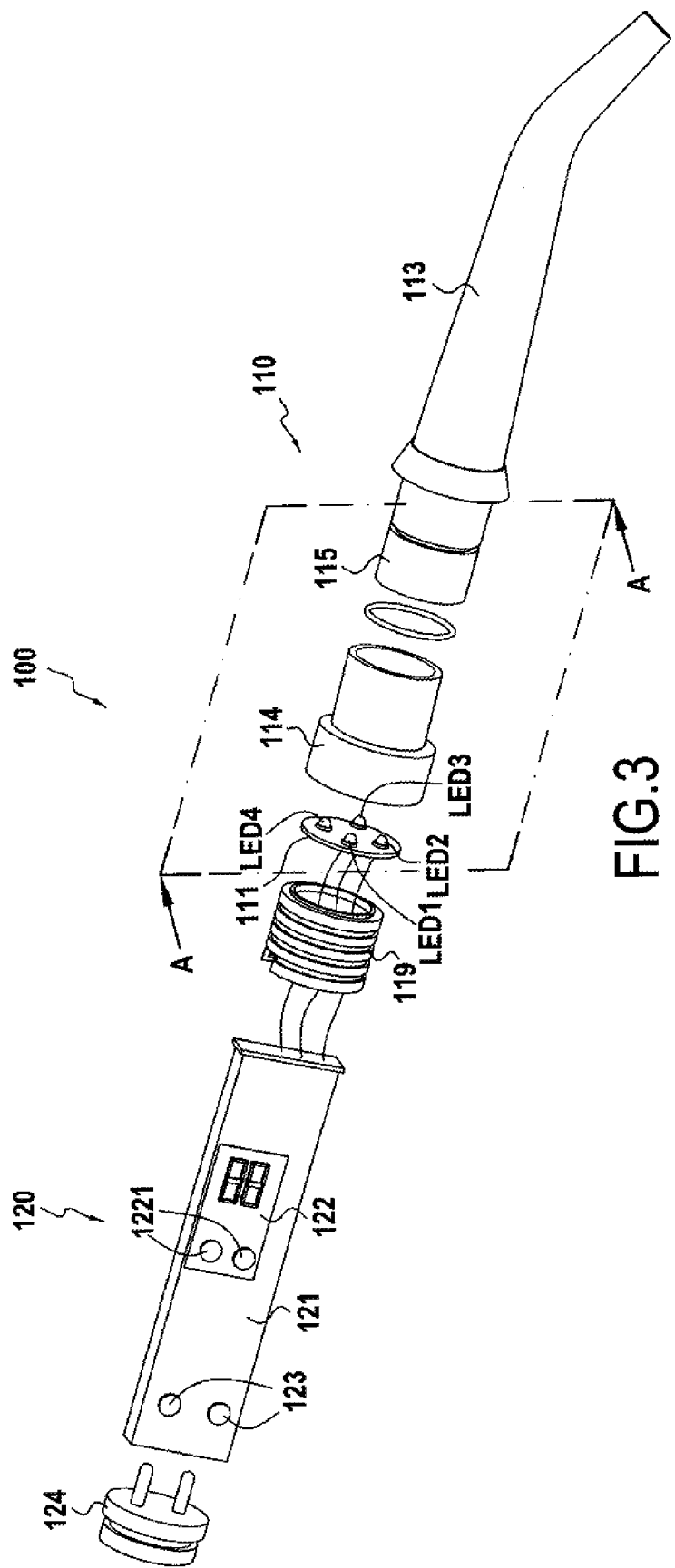
FIG. 3 is an exploded view in perspective showing the component elements of a photo-curing appliance in accordance with an embodiment of the invention.

FIG. 3 shows the component elements of a photo-curing device 100 such as the device shown in FIG. 2, for example, in accordance with an embodiment of the invention. The photo-curing device 100 comprises an anterior portion 110 having a light source or optical block 111 fitted with four light-emitting diodes LED1, LED2, LED3, and LED4, each emitting light in a respective determined wavelength range.

The LEDs LED1 to LED4 are coupled to a waveguide 113 serving to guide, aim, and emit the light energy produced by the LEDs LED1 to LED4 towards a lighting zone corresponding to the photo-curable material that is to be activated. The waveguide 113 and the optical block 111 are coupled together by means of an element 114, the waveguide 113 being removably mounted on one end of the element 114, and the optical block 111 being mounted on the other end of the element 114 via a support element 119.

The waveguide 113 may be constituted by fused optical fibers, by a set of lenses, by a rigid tube of optical material, or by a liquid optical fiber.

Figure 4:
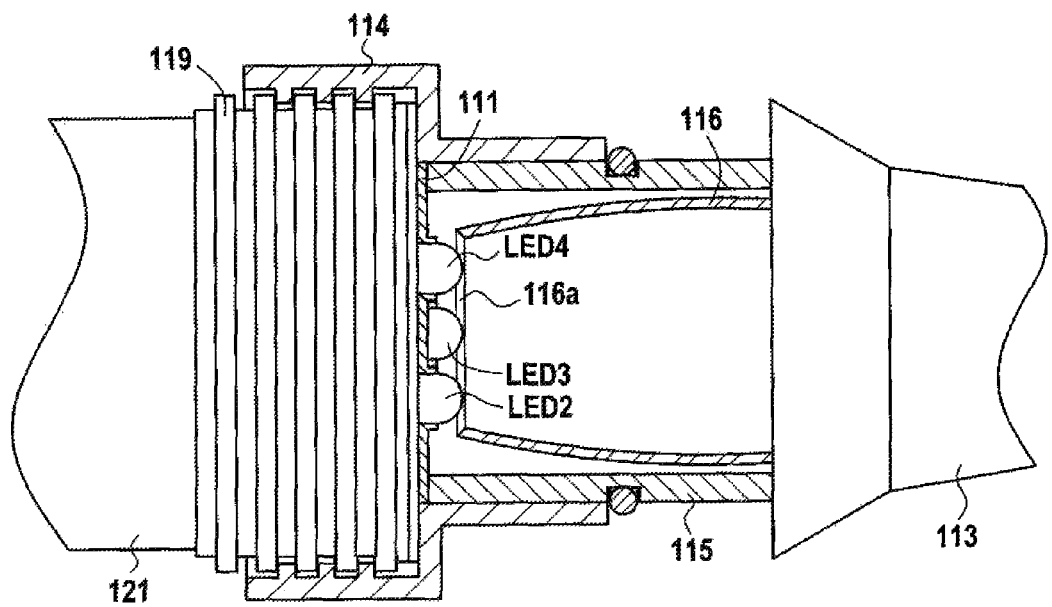
FIG. 4 is a fragmentary section view on AA of FIG. 3.

The waveguide 113 is associated with and guided by the element 114 by means of an endpiece 115 that, as shown in FIG. 4, includes internally a reflector 116 serving to reduce the divergence of the radiation emitted by the LEDs LED1 to LED4 and including a central opening 116*a* for housing them.

Figure 1:
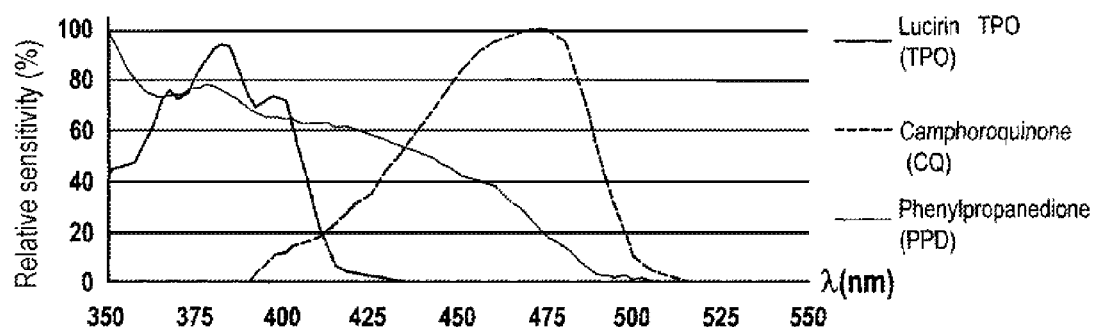
FIG. 1 is a graph showing examples of sensitivity spectra for various photo-initiators.

The photo-curing device 100 has a second portion that corresponds to a control unit 120 and that is situated immediately beneath the anterior portion 110. This control unit 120 includes a card 121 fitted on one face with a screen 122 having operating and safety indicators 1221 together with control buttons 123, and on its other face an electronic control circuit (not shown in FIG. 1). The control unit is connected via connector means 124 to an electrical power supply that may be constituted in particular by an independent power supply comprising rechargeable batteries, or an external power supply connected to mains, or indeed a local power supply available on a practitioner's dentistry unit. The LEDs LED1 to LED4 of the optical block 111 and the light intensity sensor 118 are electrically connected to the electronic control circuit.

Figure 5:
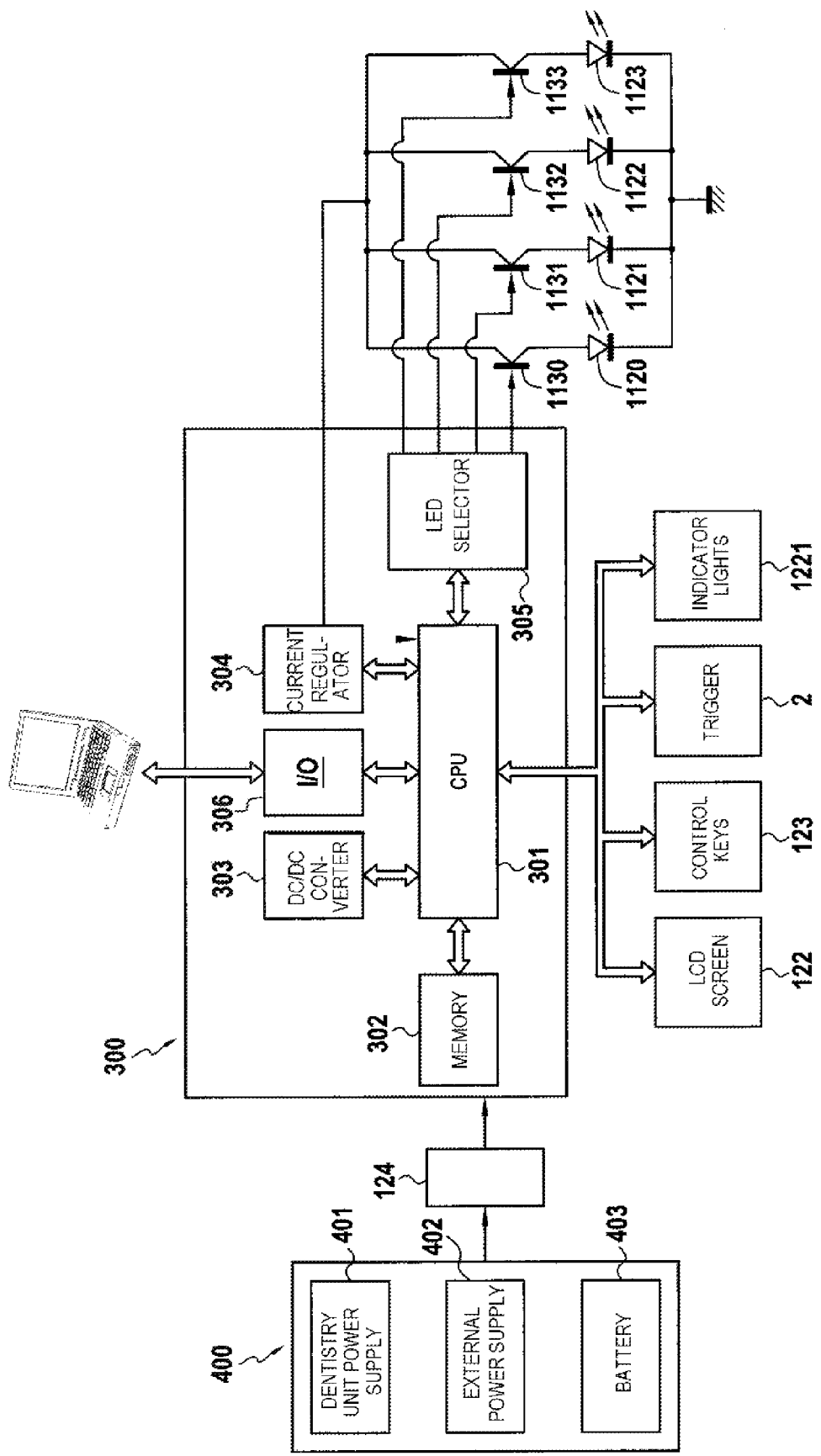
FIG. 5 is a block diagram of an electronic control circuit for a photo-polymerizing device in accordance with an embodiment of the present invention.

FIG. 5 is a block diagram of an electronic control circuit 300 in an embodiment of the photo-curing device of the invention, this circuit being located on one of the faces of the above-described card 121 of the control unit 120.

The circuit 300 comprises a central processor unit (CPU) card 301 (e.g. a programmable microcontroller) that is programmed to control all of the polymerization parameters. This card includes a non-volatile memory 302 (e.g. an electrically erasable programmable read only memory (EEPROM)) that contains, in the form of menus that are selectable and optionally modifiable via a downloading interface 306, the photo-curing parameters for application in each menu. Specific menus in accordance with the invention are described below.

Using the liquid crystal display (LCD) screen 122, and the control buttons 123, the practitioner selects one of the proposed menus and then triggers the photo-curing cycle by means of the trigger or trigger button 2 (cf. FIG. 2).

The CPU card 301 controls selective activation of the LEDs LED1 to LED4 of the optical block 111 and controls the power they deliver. The CPU card 301 sets the parameters of and controls a pulse width modulated (PWM) direct current/direct current (DC/DC) converter 303, thereby making it possible to minimize the temperature rises generated in the handpiece. A current regulator 304 continuously servo-controls the energy delivered to the LEDs LED1 to LED4.

Concerning selective activation of the LEDs for scanning over a broad spectrum in accordance with the invention, the CPU card 301 controls activation of each LED LED1 to LED4 via a diode selector 305 that, as a function of the control signals it receives from the CPU card, activates one or other of the LEDs. In the embodiment described, the selective activation of the LEDs is implemented by means of transistors 1130 to 1133 connected to the output of the current regulator 304 with the on/off states of the transistors being controlled by the selector 305.

The circuit 300 is connected via the connector means 124 to an electrical power supply 400 that may equally well be a power supply 401 forming part of a dental unit, an external power supply 402 such as the mains, or an independent power supply using a battery 403, e.g. a battery of the Li-Ion, In—Cd, MnAl, etc. type that is rechargeable by induction, by contact, etc.

Figure 6:
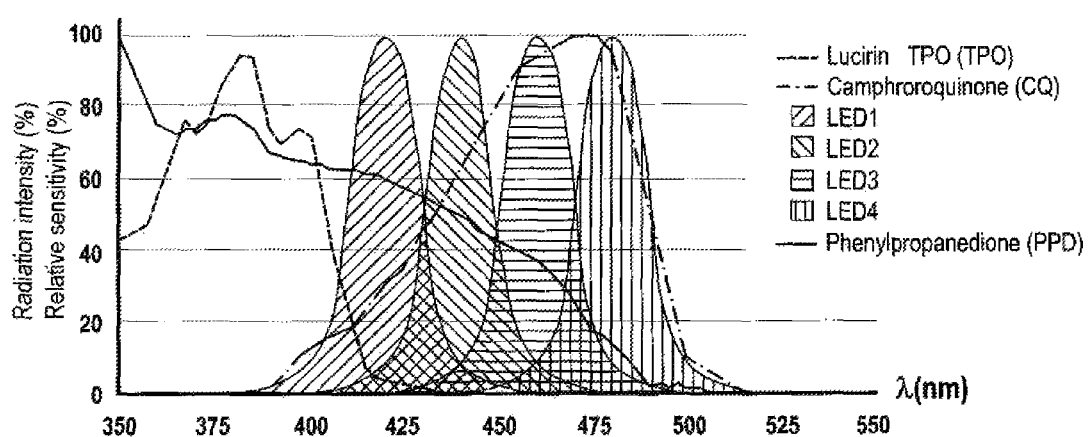
FIG. 6 is a graph showing an extended wavelength range obtained by uniting the emission spectra of four LEDs.

In the example described, the four LEDs LED1 to LED4 emit light in respective emission spectra or wavelength ranges SpA, SpB, SpC, and SpD, as shown in FIG. 6. More precisely, the emission spectrum of LED1 is centered on the wavelength of 420 nm, the emission spectrum of LED2 is centered on the wavelength of 440 nm, the emission spectrum of LED3 is centered on the wavelength of 460 nm, and the emission spectrum of LED4 is centered on the wavelength of 480 nm. This covers a continuous wavelength range extending from 400 nm to 500 nm (or for 410 nm to 490 nm for radiation intensity ≥50%), thereby covering the target wavelength spectra of photo-initiators such as camphoroquinone (CQ), phenylpropanedione (PPD), and lucirin, at least in part.

As shown in FIG. 6, the adjacent emission spectra (i.e. SpA & SpB, SpB & SpC, and SpC & SpD) overlap in part so as to cover an entire emission spectrum or wavelength range that extend continuously from the first wavelengths covered by the LED 1120 to the last wavelengths covered by the LED 1123.

The emission spectra preferably overlap at wavelengths that correspond substantially to 50% of the intensity of the radiation emitted by each LED. This ensures radiation having at least a minimum intensity of 50% over an entire continuous wavelength length, here extending from 410 nm to 490 nm.

In accordance with the invention, the LEDs are activated, i.e. powered, selectively one after another. This selective activation of the LEDs may be implemented in various orders (LED selection) with various constant or varying power supply parameters for the LEDs.

Example activation programs or profiles for photo-curing are described below. These photo-curing profiles may be selected using downloaded or prerecorded menus in the memory 302 of the electronic control circuit 300. Each corresponds to a determined period of time, referred to as the "activation" period, during which predefined (optional periodic) activation sequences of the diodes are operated.

Figure 8:
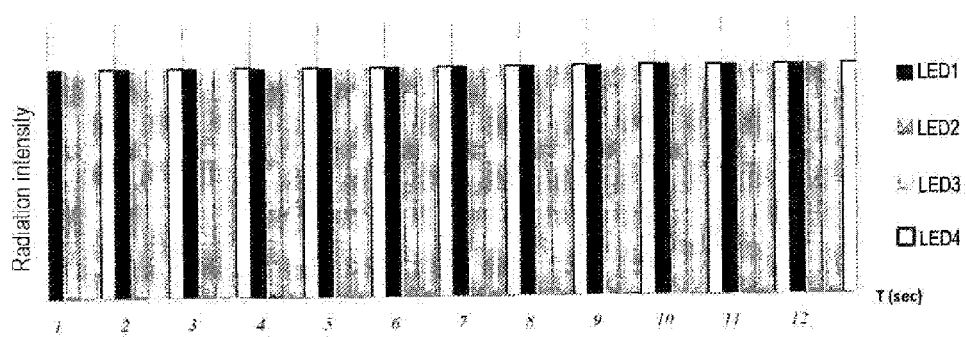

FIG. 8 shows a first element of a photo-curing profile in which the same sequence is repeated several times over (here 12 times) during the activation period, the profile consisting in activating each of the LEDs LED1 to LED4 at a constant power level for a determined time interval (here 1 second). With such a profile, the entire wavelength range covered by the emission spectra of the four LEDs is scanned during each sequence. Scanning is thus performed over a wavelength range that is continuous and broad, even in the event of the profile being interrupted after only one sequence (here having a duration of 1 second).

Figure 7:
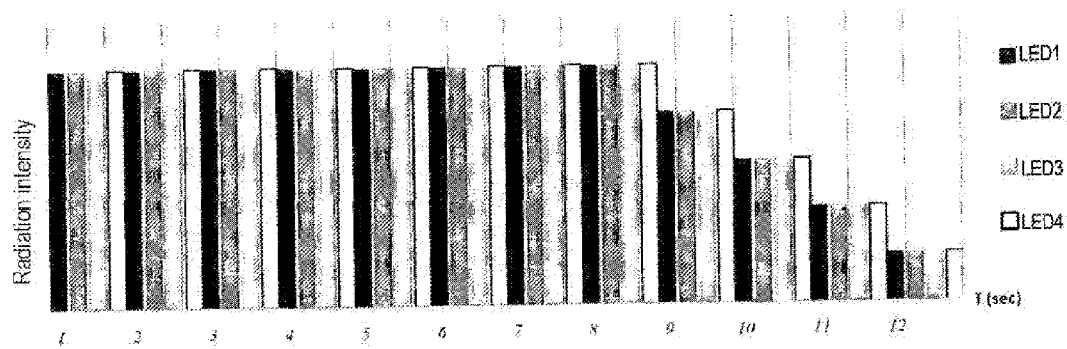
FIGS. 7 to 9 show examples of program profiles for selectively activating the LEDs that can be implemented using the photo-curing appliance of the invention.

FIG. 7 shows a second example of a photo-curing profile that differs from the first described above in that the power delivered to the LEDs is reduced progressively (by reducing the power supply current delivered thereto) during the last few sequences (here the last four sequences). In this activation profile the radiation heat emitted by the LEDs is reduced towards the end of the activation profile, thereby limiting the increase in temperature that occurs at the end of the cycle since it is additional to the exothermic cross-linking or polymerization reaction that takes place in the exposed material. When material is being cured on a patient, e.g. in the field of dentistry, the sensation of an excessive rise in temperature felt by the patient can thus be decreased and patient comfort improved.

Figure 9:
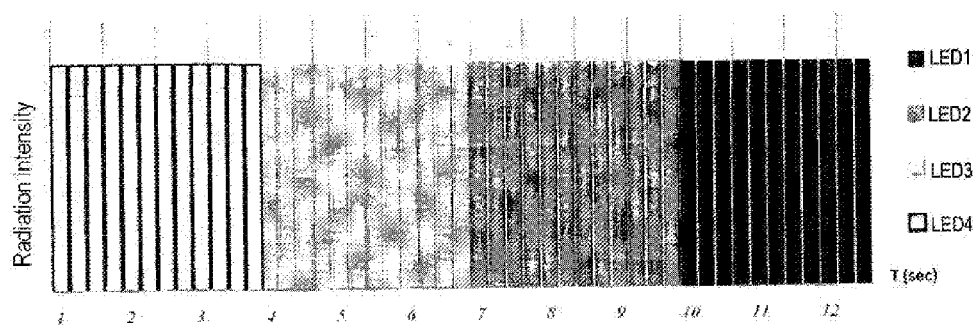

FIG. 9 shows a third example of a photo-curing profile that comprises four sequences, in each of which only one LED is activated, with the order of sequences being determined in such a manner as to begin the activation period by activating the diodes that emit the most radiation heat and at the end of the activation period the diodes that emit the least radiation heat. This avoids an excessive rise in temperature at the end of the cycle in addition to the heat given off by the exothermic cross-linking or polymerization reaction of the exposed material. Patient comfort is thus improved.

The photo-curing device is not limited to the embodiment described above. In particular, the use of a waveguide is not essential, for example when LEDs are used that are encapsulated in a module that includes an incorporated lens.

Furthermore, the photo-curing device of the invention is not limited to movable appliances such as a handpiece for use in the field of dentistry. In particular, it may be in the form of a bench appliance forming a stationary exposure zone in which the material for photo-curing is placed, such as for example a coating for fingernails.

The invention claimed is:

1. A photo-curing device comprising a light source configured to initiate curing of a photo-curable material,
said light source comprising at least two light-emitting diodes, each diode emitting light in a determined wavelength range, the wavelength ranges of said at least two LEDs overlapping partially so as to cover a continuous wavelength range that is broader than the wavelength range of each of the LEDs, and
wherein the photo-curing device comprises an activation device arranged to selectively activate each LED,
the device further comprising a controller arranged to successively activate each of the LEDs a plurality of times in a cycle and to progressively reduce the power delivered to each of the LEDs at the end of the cycle.

2. The device according to claim 1, comprising at least one waveguide arranged to either or both guide or aim light radiation emitted by the LEDs towards a zone for treatment.

3. The device according to claim 1, comprising a connector arranged to receive electrical power from at least one of the following power supplies: a self-contained power supply and a dental unit.

4. The device according to claim 1, further comprising a switch arrangement configured to selectively power each of said LED from a single power supply.

5. The device according to claim 1, further comprising a controller arranged to successively activate each of the LEDs at least once in a determined time interval.

6. The device according to claim 1, wherein emission spectra of each of the said at least two LEDs overlap at wavelengths that correspond to at least 50% of the intensity of the radiation emitted by each of the LEDs.

7. The device according to claim 1, wherein radiation emitted by the LEDs has at least a minimum intensity of 50% over a combined continuous range of wavelength length of the LEDs.

8. A photo-curing device comprising a light source configured to initiate curing of a photo-curable material,
said light source comprising at least two light-emitting diodes, each diode emitting light in a determined wavelength range, the wavelength ranges of said at least two LEDs overlapping partially so as to cover a continuous wavelength range that is broader than the wavelength range of each of the LEDs, and
wherein the photo-curing device comprises an activation device arranged to selectively activate each LED,
the device further comprising a controller arranged to successively activate each LED over a determined activation period, said controller arranged to activate the LED that emits a greatest radiation heat at the beginning of the activation period and to activate the LED that emits a least radiation heat at the end of the activation period.

9. The device according to claim 8, further comprising a switch arrangement configured to selectively power each of said LED from a single power supply.

10. The device according to claim 8, further comprising a controller arranged to successively activate each of the LEDs at least once in a determined time interval.

11. The device according to claim 8, wherein emission spectra of each of the said at least two LEDs overlap at wavelengths that correspond to at least 50% of the intensity of the radiation emitted by each of the LEDs.

12. The device according to claim 8, wherein radiation emitted by the LEDs has at least a minimum intensity of 50% over a combined continuous range of wavelength length of the LEDs.

13. The device according to claim 8, further comprising at least one waveguide arranged to either or both guide or aim light radiation emitted by the LEDs towards a zone for treatment.

14. The device according to claim 8, further comprising a connector arranged to receive electrical power from at least one of the following power supplies: a self-contained power supply and a dental unit.

15. A photo-curing device comprising a light source configured to initiate curing of a photo-curable material,
said light source comprising a plurality of light-emitting diodes (LEDs), each of the LEDs emitting light in a determined wavelength range, the wavelength ranges of at least two of the LEDs overlapping partially so as to cover a continuous wavelength range that is broader than the wavelength range of each of the two LEDs, and
wherein the photo-curing device comprises an activation device arranged to selectively activate each of the LEDs,
the plurality of LEDs includes at least four LEDs having respective emission spectra centered on about 420 nm, 440 nm, 460 nm, and 480 nm so as to cover a continuous wavelength range extending from at least 410 nm to 490 nm; and
the device further comprising a switch arrangement configured to selectively power each of the LEDs from a single power supply such that at least one of the four LEDs is not powered while at the same time at least another of the four LEDs is powered,
wherein the photo-curing device further comprises a controller arranged to separately and successively activate each of the LEDs at least once in a determined time interval.

16. The device according to claim 15, wherein emission spectra of each of the said at least two LEDs overlap at wavelengths that correspond to at least 50% of the intensity of the radiation emitted by each of the LEDs.

17. The device according to claim 15, wherein radiation emitted by the LEDs has at least a minimum intensity of 50% over a combined continuous range of wavelength length of the LEDs.

* * * * *